(12) United States Patent
Kiiski et al.

(10) Patent No.: US 10,947,457 B2
(45) Date of Patent: Mar. 16, 2021

(54) PRODUCTION OF A FUEL COMPOSITION

(71) Applicant: Neste Oyj, Espoo (FI)

(72) Inventors: Ulla Kiiski, Porvoo (FI); Marina Lindblad, Porvoo (FI); Marja Tiitta, Porvoo (FI); Kaija Isokoski, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/470,867

(22) PCT Filed: Dec. 13, 2017

(86) PCT No.: PCT/EP2017/082660
§ 371 (c)(1),
(2) Date: Jun. 18, 2019

(87) PCT Pub. No.: WO2018/114534
PCT Pub. Date: Jun. 28, 2018

(65) Prior Publication Data
US 2020/0087578 A1    Mar. 19, 2020

(30) Foreign Application Priority Data
Dec. 23, 2016 (FI) ...................... 20166034

(51) Int. Cl.
C10G 3/00 (2006.01)
C10L 1/18 (2006.01)

(52) U.S. Cl.
CPC .............. *C10G 3/46* (2013.01); *C10G 3/50* (2013.01); *C10L 1/1802* (2013.01); *C10G 2300/304* (2013.01); *C10G 2400/04* (2013.01); *C10G 2400/30* (2013.01)

(58) Field of Classification Search
CPC ...... C10G 3/46; C10G 3/50; C10G 2300/304; C10G 2400/04; C10G 2400/30; C10G 2300/308; C10G 3/44; C10L 1/1802; C10L 1/08; Y02E 50/13; Y02P 30/20; C07C 1/20; C07D 307/38
USPC ........ 585/240, 241, 242, 319, 317, 318, 332
See application file for complete search history.

(56) References Cited

U.S. PATENT DOCUMENTS

| 3,287,374 A | 11/1966 | Dunlop et al. |
| 5,454,842 A | 10/1995 | Poirier et al. |
| 2007/0010682 A1 | 1/2007 | Myllyoja et al. |
| 2012/0316372 A1 | 12/2012 | Corma Canos et al. |
| 2013/0144090 A1 | 6/2013 | Pansare et al. |
| 2013/0144091 A1 | 6/2013 | Pansare et al. |
| 2013/0144094 A1 | 6/2013 | Pansare et al. |
| 2013/0144098 A1 | 6/2013 | Pansare et al. |
| 2013/0158315 A1 | 6/2013 | Corma et al. |
| 2013/0237728 A1 | 9/2013 | Lotero et al. |

FOREIGN PATENT DOCUMENTS

| CA | 2163916 A1 | 6/1996 |
| CN | 101679874 A | 3/2010 |
| CN | 103189475 A | 7/2013 |
| EP | 2584022 A1 | 4/2013 |

OTHER PUBLICATIONS

Avelino Corma et al., "Production of High-Quality Diesel from Biomass Waste Products", Angewandte Chemie International Edition, vol. 50, No. 10, Jan. 31, 2011, pp. 2375-2378.
Finnish Search Report dated Apr. 21, 2017.
International Search Report (PCT/ISA/210) dated Jun. 6, 2018, by the European Patent Office as the International Searching Authority for International Application No. PCY/EP2017/082660.
M. Acaroglu et al., "Relationships between Viscosity and Density Measurements of Biodiesel Fuels", Energy Sources, Part A, Recovery, Utilization and Environmental Effects, vol. 29, No. 8, Apr. 11, 2007, pp. 704-712.
S. Stournas et al., "Effects of fatty acid derivatives on the ignition quality and cold flow of diesel fuel", Journal of the American Oil Chemists' Society, vol. 72, No. 4, Apr. 1, 1995, pp. 433-437.
Yati Indri et al., "Water-promoted selective heterogeneous catalytic trimerization of xylose-derived 2-methylfuran to diesel precursors", Applied Catalysis A: vol. 495, Feb. 12, 2015, pp. 200-205.
M.V. Landau et al., "Medium Severity Hydrotreating and Hydrocracking of Israeli Shale Oil—III Hydrocracking of Hydrotreated Shale Oil and Its Atmospheric Residue for Full Conversion to Motor Fuels", Fuel, Nov. 1, 1998, vol. 77, No. 14, pp. 1589-1597, XP004287107.
Office Action (Communication) dated Nov. 26, 2020, by the European Patent Office in corresponding European Patent Application No. 17829165.4. (4 pages).

*Primary Examiner* — Thuan D Dang
(74) *Attorney, Agent, or Firm* — Buchanan Ingersoll & Rooney PC

(57) ABSTRACT

The present invention relates to a method for production of a fuel composition, more specifically a middle distillate fuel composition, and a composition—in particular a co feed composition comprising a furanyl containing oligomerisation composition admixed with one or more material component comprising fatty acids or fatty acid derivatives and the use of such composition.

12 Claims, 6 Drawing Sheets

PRODUCTION OF A FUEL COMPOSITION

TECHNICAL FIELD

The present invention relates to a method for production of a fuel composition, more specifically a middle distillate fuel composition, and a composition—in particular a co feed composition comprising a furanyl containing oligomerisation composition admixed with one or more material component comprising fatty acids or fatty acid derivatives and the use of such composition.

BACKGROUND ART 2-methylfuran (2-MF)—is a platform molecule that can be produced by selective hydrogenation of C5-sugar derived furfural. Catalytic upgrading of 2-MF includes a carbon chain increase step by oligomerisation and an oxygenation removal step to obtain the final hydrocarbon fuel component.

Trimerisation of 2-MF by hydroalkylation/alkylation reactions using sulfuric acid (aq.) as catalyst is disclosed in literature "A. Corma, O. de la Torre, M. Renz and N. Villandier, "Production of high-quality diesel from biomass waste products", Angew. Chem. Int. Ed. 50 (2011) 2375-2378" and in patent publication US 2012/0316372 A1, where a physical mixture of Pt/C and Pt/TiO$_2$ is used as a catalysts (at 350° C. and 50 bar) whereby a product comprising as the major part hydrocarbons that were classified as linear, branched and monocyclic compounds are produced.

In "A. Corma, O. de la Torre, M. Renz and N. Villandier, "Production of high-quality diesel from biomass waste products", Angew. Chem. Int. Ed. 50 (2011) 2375-2378" the trimerisation is highly controlled whereby primarily bisylvylalkane molecules with 14 carbon atoms are formed. The following hydrodeoxygenation primarily gives linear, branched and monocyclic compounds.

The selectivity towards trimer or tetramer formation with 2-MF on a resin catalyst (Amberlyst 15) is disclosed in "I. Yati, M. Yeom, J-W. Choi, H. Choo, D. J. Suh, J-M. Ha, "Water-promoted selective heterogeneous catalytic trimerisation of xylose-derived 2-methylfuran to diesel precursors", Appl. Catal. A: General 495 (2015) 200-205" and was reported to be controlled by the amount of water present in the reaction. Oxygen removal for trimer and tetramer products was conducted in a two-step process (with Pd/C at 140° C. and Ru/SiO$_2$—Al$_2$O$_3$ at 280° C., and 60 bar). The trimer feed was fully deoxygenated forming ~99% C$_9$-C$_{20}$ hydrocarbons while the tetramer feed was only partly deoxygenated under these conditions forming 84% C$_9$-C$_{20}$ hydrocarbons and 15% oxygenated compounds.

One of the challenges when preparing fuel compositions—having good cold flow properties and reasonable density—based on 2-methylfuran, which can afterwards be used as a blending component in a final blended fuel composition, is to control the degree of oligomerisation. However, none of the prior art methods relates to oligomerisations conditions that disclose how to obtain a furanyl containing oligomerisation composition comprising as the major part oligomers selected from trimers, tetramers and pentamers of 2-MF comprising from 2 to 4 furanyl moieties. Another challenge in preparing fuel compositions which can afterwards be used as a blending component in a final blended fuel composition is to successfully remove oxygen from the oligomerisation product.

Thus, there remains a need for further methods for production of fuel compositions based on 2-methylfuran that has excellent blending properties so that it can be used as a blending component in a final blended fuel composition.

SUMMARY OF INVENTION

The present invention was made in view of the prior art described above, and the object of the present invention is to provide a method for production of a fuel composition based on 2-methylfuran (2-MF).

Another object of the present invention is to produce a fuel composition (e.g. a middle distillate composition) based on 2-methylfuran (2-MF) that has good cold flow properties so that a following isomerisation step is not needed and also has reasonable density properties.

Still another object of the present invention is to produce a fuel composition (e.g. a middle distillate composition) based on 2-methylfuran (2-MF) that has excellent blending properties so that it can be used as a blending component to be blended with a diesel hydrocarbon composition (e.g. paraffinic renewable diesel or a gas-to-liquid (GTL) diesel) in a final blended fuel composition where the final blended fuel composition will have improved cold flow properties, acceptable cetane number and increased density compared to the diesel hydrocarbon composition itself.

To solve the problem, the present invention provides a method for production of a fuel composition, the method comprising the steps of: a) oligomerisation of 2-methylfuran (2-MF) using an acidic catalyst resulting in a furanyl containing oligomerisation composition comprising at least 70 wt. % oligomers selected from the group of trimers, tetramers and pentamers of 2-MF comprising from 2 to 4 furanyl moieties; b) optionally admixing one or more material component comprising fatty acids or fatty acid derivatives to the furanyl containing oligomerisation composition from step a) creating a co-feed composition; c) subjecting the furanyl containing oligomerisation composition from step a) or the co-feed composition from step b) to a hydrodeoxygenation treatment in a hydrodeoxygenation unit comprising a molybdenum and/or tungsten catalyst optionally a promoted molybdenum and/or tungsten catalyst, optionally a sulfided molybdenum and/or tungsten catalyst, resulting in a fuel composition; where said fuel composition comprises at least 55 wt. % of both mono- and di-naphthenes and aromatics in a part of the fuel composition resulting from the hydrodeoxygenation treatment of the furanyl containing oligomerisation composition.

That is, the inventors of the present invention in a first aspect of the invention found that the quality of the fuel composition can be improved by using specific process conditions. By the use of an acidic catalyst in the oligomerisation step and thereby controlling the degree of oligomerisation of 2-methylfuran (2-MF)—a furanyl containing oligomerisation composition comprising at least 70 wt. % oligomers selected from the group of trimers, tetramers and pentamers of 2-MF comprising from 2 to 4 furanyl moieties was produced. By further treating the furanyl containing oligomerisation composition to a molybdenum and/or tungsten catalyst, optionally a promoted molybdenum and/or tungsten catalyst, optionally a sulfided molybdenum and/or tungsten catalyst, in the hydrodeoxygenation treatment—a fuel composition with reasonable density and excellent cold properties was produced comprising relatively high amount of both mono- and di-naphthenes and aromatics in the part of the fuel composition resulting from the hydrodeoxygenation treatment of the furanyl containing oligomerisation composition.

By the use of an acidic catalyst in the oligomerisation step followed by the use of a molybdenum and/or tungsten catalyst, optionally a promoted molybdenum and/or tungsten catalyst, optionally a sulfided molybdenum and/or tungsten catalyst, in the hydrodeoxygenation step, a fuel composition having reasonable density and good cold properties is accomplished. This hydrotreated oligomerized 2MF fuel composition is a good blending component that can be blended with a diesel hydrocarbon composition (e.g. paraffinic renewable diesel or a gas-to-liquid (GTL) diesel) which has excellent cold flow properties and cetane number. When blending the fuel composition manufactured according to the present method with a diesel hydrocarbon composition (e.g. paraffinic renewable diesel or a gas-to-liquid (GTL) diesel), the two components complement each other giving the blend composition increased density compared to the diesel hydrocarbon composition itself. The density of the blend can be increased to a level required in EN590. In addition, the blend composition will also have improved cold flow properties and a good cetane number.

In table 2 it is shown that the cloud point (measured by the ASTM D7689 method) was <−95° C., which indicates good cold flow properties of the fuel composition manufactured by the present invention. Since the fuel composition has good cold flow properties it can be used directly as a drop-in fuel thereby eliminating the need for having an isomerisation step as part of the method. This is both economy saving and time saving in large fuel production plants. The fuel composition has reasonable cetane number bCN 46, and when blended with a diesel hydrocarbon composition (e.g. paraffinic renewable diesel or a gas-to-liquid (GTL) diesel) the cetane number will be above 51, which is the minimum in EN590.

Due to the use of an acidic catalyst in the oligomerisation step followed by the use of a molybdenum and/or tungsten catalyst, optionally a promoted molybdenum and/or tungsten catalyst, optionally a sulfided molybdenum and/or tungsten catalyst, in the hydrodeoxygenation step, a fuel composition having relatively high amount of mono- and di-naphthenes and aromatics in the fuel composition results which may increase both density and improve the cold flow properties of the fuel composition. By the method according to the present invention, density was ~830 kg/m$^3$ (at 15° C., measured by the ENISO 12185 method). When the 2MF based component of the present invention is blended with a diesel hydrocarbon composition (e.g. paraffinic renewable diesel or a gas-to-liquid (GTL) diesel) density minimum of EN590 can be reached.

So with the method according to the present invention it is possible to achieve both improved cold flow properties and increased density of the final blend fuel composition. Compared to and used together with a diesel hydrocarbon composition (e.g. paraffinic renewable diesel or a gas-to-liquid (GTL) diesel), the produced 2MF component fuel composition increases the density while the diesel hydrocarbon composition improves cold properties. The specific properties of the blend composition depends also on the properties of the diesel hydrocarbon composition with which the 2-MF component is blended.

In some cases, the fuel composition may comprise minor amount of oxygenate residue which may help improve the lubricity of the fuel composition and also of the final blend fuel composition.

Step b can be mandatory.

The inventors has found that when one or more material component comprising fatty acids or fatty acid derivatives are admixed to the furanyl containing oligomerisation composition from step a) thereby creating a co-feed composition, the cold flow properties and the density is further improved compared to when no material component comprising fatty acids or fatty acid derivatives are admixed to the furanyl containing oligomerisation composition from step a). Hydrogenated fatty acids and fatty acid derivatives are straight-chain hydrocarbons which have high cetane numbers. When mixing the fatty acids or fatty acid derivatives to the furanyl containing oligomerisation composition from step a) a fuel product having a relatively high cetane number can be achieved. In addition, the fuel composition arising from using the co-feed composition can have excellent cold flow properties. Since the fuel composition can have excellent cold flow properties it can be used directly as a drop-in fuel thereby eliminating the need for having an isomerisation step as part of the method.

The fuel composition may be a middle distillate fuel composition.

The fuel composition may be a drop-in fuel composition.

The one or more material component comprising fatty acids or fatty acid derivatives may be selected from plant oil/fats including crude tall oil or tall oil fatty acids, vegetable oil/fats, animal oil/fats including fish oil/fats and algae oil/fats, or oil/fats from other microbial processes, for example genetically manipulated algae oil/fats, genetically manipulated oil/fats from other microbial processes and also genetically manipulated vegetable oil/fats, recyclable waste recyclable residue, or a combination thereof.

The oligomerisation of 2-methylfuran (2-MF) in step a) may results in a furanyl containing oligomerisation composition comprising at least 80 wt. % oligomers selected from the group of trimers, tetramers and pentamers of 2-MF comprising from 2 to 4 furanyl moieties.

More than 60 wt % of the fuel composition may have a boiling point range of 150-400° C., such as 180-400° C. or such as 180-360° C.

It may be that no isomerisation reactions are conducted to the fuel composition.

The acidic catalyst in step a) may be an acid ion exchange resin catalyst, such as a polystyrene-co-divinylbenzene sulfonic acid resin catalyst.

The molybdenum and/or tungsten catalyst in step c) may be promoted with nickel or cobalt.

The promoted molybdenum and/or tungsten catalyst in step c) may be a sulfided NiMo-catalyst.

In the method step c) may be carried out under reaction conditions of temperature between 200-400° C., such as between 220-380° C., such as between 250-350° C., such as between 295-335° C. and at between 20 to 150 bar, such as between 60 to 120 bar, such as between 90-110 bar, such as between 95-100 bar.

The present invention also discloses a co-feed composition. Therefore, in accordance with the above description, there is also provided a composition comprising a furanyl containing oligomerisation composition comprising at least 70 wt. % oligomers selected from the group of trimers, tetramers and pentamers of 2-MF comprising from 2 to 4 furanyl moieties admixed with one or more material component comprising fatty acids or fatty acid derivatives.

The inventors have found that when one or more material component comprising fatty acids or fatty acid derivatives are admixed to the furanyl containing oligomerisation composition thereby creating a co-feed composition for the following HDO treatment, the cold flow properties and the density of the fuel composition is further improved compared to when no material component comprising fatty acids or fatty acid derivatives are admixed to the furanyl containing oligomerisation composition from step a). Hydrogenated fatty acids and fatty acid derivatives are straight-chain hydrocarbons which have high cetane numbers. When mixing the fatty acids or fatty acid derivatives with the furanyl containing oligomerisation composition a fuel product having a relatively high cetane number can be achieved. In addition, the fuel composition arising from using the co-feed composition can have very good cold flow properties. Since the fuel composition can have excellent cold flow properties it can be used directly as a drop-in fuel. Additionally there might be no need for isomerisation.

The majority of the trimers, tetramers and pentamers may be selected from one or more of the following components or their isomers:

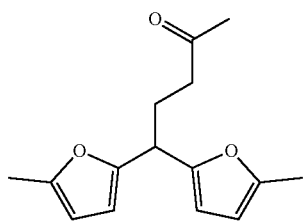

5,5-di-(5-methyl-2-furanyl)-2-pentanone
C$_{15}$H$_{18}$O$_3$ (MW 246 amu)

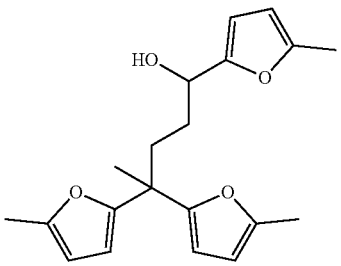

1-hydoxy-1,4,4-tri-(5-methyl-2-furanyl)-pentane,
C$_{20}$H$_{24}$O$_4$ (MW 328 amu)

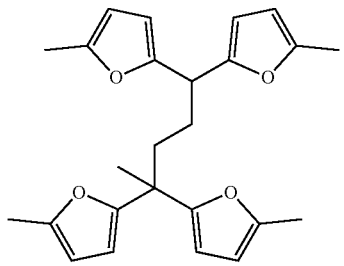

2,2,5,5-tetra-(5-methyl-2-furanyl)-pentane
C$_{25}$H$_{28}$O$_4$ (MW 329 amu)

Different isomers of these trimers, tetramers and pentamers may be possible, such as for example:

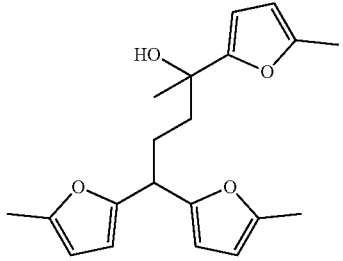

The one or more material component comprising fatty acids or fatty acid derivatives may represent a majority of the composition. The composition may comprise from 50 to 90 wt. % of one or more material component comprising fatty acids or fatty acid derivatives.

The one or more material component comprising fatty acids or fatty acid derivatives may be selected from plant oil/fats including crude tall oil or tall oil fatty acids, vegetable oil/fats, animal oil/fats including fish oil/fats and algae oil/fats, or oil/fats from other microbial processes, for example genetically manipulated algae oil/fats, genetically manipulated oil/fats from other microbial processes and also genetically manipulated vegetable oil/fats, recyclable waste recyclable residue, or a combination thereof.

In another aspect of the present invention, there is also provided the use of a composition as presented in this application as a blending component for increasing the density of a blend composition comprising a diesel hydrocarbon composition. The diesel hydrocarbon composition can be a middle distillate fuel composition such as a paraffinic renewable diesel or a gas-to-liquid (GTL) diesel.

That is, the composition as presented in this application can be used as a density improver in a middle distillate fuel composition such as a paraffinic renewable diesel or a gas-to-liquid (GTL) diesel.

In another aspect of the present invention, there is also provided the use of a composition as presented in this application as a blending component for improving the cold flow properties of a blend composition comprising a diesel hydrocarbon composition. The diesel hydrocarbon composition can be a middle distillate fuel composition such as a paraffinic renewable diesel or a gas-to-liquid (GTL) diesel.

That is, the composition as presented in this application can be used as a cold flow property improver in a middle distillate fuel composition such as a paraffinic renewable diesel or a gas-to-liquid (GTL) diesel.

The hydrotreated oligomerized 2MF fuel composition is a good blending component that can be blended with a diesel hydrocarbon composition (e.g. paraffinic renewable diesel or a gas-to-liquid (GTL) diesel) which has excellent cold flow properties and cetane number. When blending the fuel composition manufactured according to the present method with a diesel hydrocarbon composition (e.g. paraffinic renewable diesel or a gas-to-liquid (GTL) diesel), the two components complement each other giving the blend composition increased density compared to the diesel hydrocarbon composition itself. The density of the blend can be increased to a level required in EN590. In addition, the blend composition will also have improved cold flow properties and a good cetane number.

In another aspect of the present invention, there is also provided the use of a furanyl containing oligomerisation composition comprising at least 70 wt. % oligomers selected from the group of trimers, tetramers and pentamers of 2-MF comprising from 2 to 4 furanyl moieties as a co-feed in an existing refinery hydro-treating unit.

The furanyl containing oligomerisation composition can be admixed with one or more material component comprising fatty acids or fatty acid derivatives thereby creating a co-feed composition for the following HDO treatment. The cold flow properties and the density of the fuel composition may be further improved compared to when no material component comprising fatty acids or fatty acid derivatives are admixed to the furanyl containing oligomerisation. When mixing the fatty acids or fatty acid derivatives with the furanyl containing oligomerisation composition a fuel product having a relatively high cetane number can be achieved. In addition, the fuel composition arising from using the co-feed composition can have very good cold flow properties. Since the fuel composition can have excellent cold flow properties it can be used directly as a drop-in fuel. Additionally there might be no need for isomerisation.

In accordance with the above description, there is also provided a fuel composition obtainable by the method according to the present invention.

In accordance with the above description, there is also provided a blend composition, the blend composition comprises a fuel composition obtainable by the method according to the present invention and a diesel hydrocarbon composition.

DETAILED DESCRIPTION OF THE INVENTION

Figure 1:
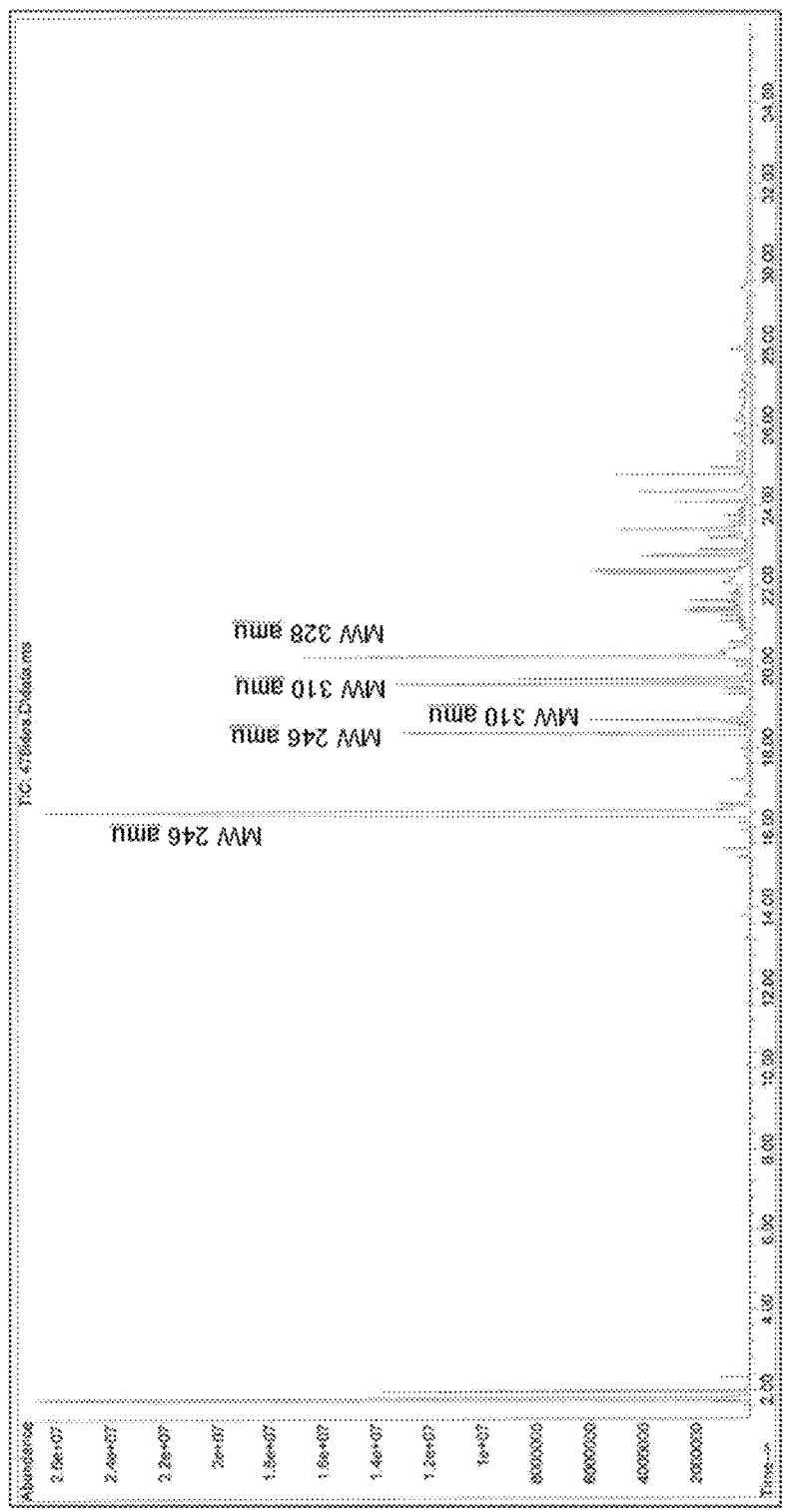
FIG. 1 shows the GC-MS identification of 2-MF condensation product formed on Amberlyst 70 where it can be seen that the oligomer distribution is trimer>>tetramer>pentamer. Traces of oligomers higher than pentamers are also seen in in this GC-MS.

In describing the aspects of the invention specific terminology will be resorted to for the sake of clarity. However, the invention is not intended to be limited to the specific terms so selected, and it is understood that each specific term includes all technical equivalents which operate in a similar manner to accomplish a similar purpose.

The inventors found that the quality of the fuel composition can be improved by using specific process conditions. By the use of an acidic catalyst in the oligomerisation step and thereby controlling the degree of oligomerisation of 2-methylfuran (2-MF)—a furanyl containing oligomerisation composition comprising at least 70 wt. % oligomers selected from the group of trimers, tetramers and pentamers of 2-MF comprising from 2 to 4 furanyl moieties was produced. The oligomer distribution may be trimer>>tetramer>pentamer due to the use of an acidic catalyst in the oligomerisation step and thereby controlling the degree of oligomerisation of 2-methylfuran (2-MF). Traces of oligomers higher than pentamers can also be present. By further treating the furanyl containing oligomerisation composition to a molybdenum and/or tungsten catalyst, optionally a promoted molybdenum and/or tungsten catalyst, optionally a sulfided molybdenum and/or tungsten catalyst, in the hydrodeoxygenation treatment—a fuel composition with reasonable density and excellent cold flow properties were produced comprising relatively high amount of both mono- and di-naphthenes and aromatics in the part of the fuel composition resulting from the hydrodeoxygenation treatment of the furanyl containing oligomerisation composition.

By the use of an acidic catalyst in the oligomerisation step followed by the use of a molybdenum and/or tungsten catalyst, optionally a promoted molybdenum and/or tungsten catalyst, optionally a sulfided molybdenum and/or tungsten catalyst, in the hydrodeoxygenation step, a fuel composition having reasonable density and good cold properties is accomplished. This hydrotreated oligomerized 2MF fuel composition is a good blending component that can be blended with a diesel hydrocarbon composition (e.g. paraffinic renewable diesel or a gas-to-liquid (GTL) diesel) which has excellent cold flow properties and cetane number. When blending the fuel composition manufactured according to the present method with a diesel hydrocarbon composition (e.g. paraffinic renewable diesel or a gas-to-liquid (GTL) diesel), the two components complement each other giving the blend composition increased density compared to the the diesel hydrocarbon composition itself. The density of the blend can be increased to a level required in EN590. In addition, the blend composition will also have improved cold flow properties and a good cetane number.

In table 2 it is shown that the cloud point (measured by the ASTM D7689 method) was <−95° C., which indicates good cold flow properties of the fuel composition manufactured by the present invention. Since the fuel composition has good cold flow properties it can be used directly as a drop-in fuel thereby eliminating the need for having an isomerisation step as part of the method. This is both economy saving and time saving in large fuel production plants. The fuel composition has reasonable cetane number bCN 46, and when blended with a diesel hydrocarbon composition (e.g. paraffinic renewable diesel or a gas-to-liquid (GTL) diesel) the cetane number will be above 51, which is the minimum in EN590.

Due to the use of an acidic catalyst in the oligomerisation step followed by the use of a molybdenum and/or tungsten catalyst, optionally a promoted molybdenum and/or tungsten catalyst, optionally a sulfided molybdenum and/or tungsten catalyst, in the hydrodeoxygenation step, a fuel composition having relatively high amount of mono- and di-naphthenes and aromatics in the fuel composition may results which may increase density and improve cold flow properties of the fuel composition. By the method according to the present invention, density was 830 kg/m$^3$ (at 15° C., measured by the ENISO 12185 method). When the 2MF based component of the present invention is blended with a diesel hydrocarbon composition (e.g. paraffinic renewable diesel or a gas-to-liquid (GTL) diesel) density minimum acquired by EN590 can be reached.

So with the method according to the present invention it is possible to achieve both improved cold properties and increased density of the final blend fuel composition. Compared to and used together with a diesel hydrocarbon composition (e.g. paraffinic renewable diesel or a gas-to-liquid (GTL) diesel), the produced 2MF component fuel composition improves the density while the diesel hydrocarbon composition improves cold properties. The specific properties of the blend composition depends also on the properties of the diesel hydrocarbon composition with which the 2-MF component is blended.

Accordingly here is provided a method for production of a fuel composition, the method comprising the steps of: a) oligomerisation of 2-methylfuran (2-MF) using an acidic catalyst resulting in a furanyl containing oligomerisation composition comprising at least 70 wt. % oligomers selected from the group of trimers, tetramers and pentamers of 2-MF comprising from 2 to 4 furanyl moieties; b) optionally admixing one or more material component comprising fatty acids or fatty acid derivatives to the furanyl containing oligomerisation composition from step a) creating a co-feed composition; c) subjecting the furanyl containing oligomerisation composition from step a) or the co-feed composition from step b) to a hydrodeoxygenation treatment in a hydrodeoxygenation unit comprising a molybdenum and/or tungsten catalyst, optionally a promoted molybdenum and/or tungsten catalyst, optionally a sulfided molybdenum and/or tungsten catalyst, resulting in a fuel composition; where said fuel composition comprises at least 55 wt. % of both mono- and di-naphthenes and aromatics in a part of the fuel composition resulting from the hydrodeoxygenation treatment of the furanyl containing oligomerisation composition.

In some cases, the fuel composition may comprise minor amount of oxygenate residue which may help improve the lubricity of the fuel composition and also of the final blend fuel composition.

Step b can be mandatory. The inventors has found that when one or more material component comprising fatty acids or fatty acid derivatives are admixed to the furanyl containing oligomerisation composition from step a) thereby creating a co-feed composition, the cold flow properties and the density is further improved compared to when no material component comprising fatty acids or fatty acid derivatives are admixed to the furanyl containing oligomerisation composition from step a). Hydrogenated fatty acids and fatty acid derivatives are straight-chain fatty acids which have high cetane numbers so when mixing the fatty acids or fatty acid derivatives to the furanyl containing oligomerisation composition from step a) a fuel product having a relatively high cetane number can be achieved. In addition, the fuel composition arising from using the co-feed composition can have very good cold flow properties. Since the fuel composition can have good cold flow properties it can be used directly as a drop-in fuel thereby eliminating the need for having an isomerisation step as part of the method.

The furanyl containing oligomerisation composition differs from other feedstock material component comprising fatty acids or fatty acid derivatives in at least one parameter, namely that the furanyl containing oligomerisation composition is substantially free of impurities (catalyst poisons) and hence there is no need to include any purification step such as degumming or bleaching to purify the furanyl containing oligomerisation composition before the hydrodeoxygenation (HDO) treatment.

The one or more material component comprising fatty acids or fatty acid derivatives may be selected from plant oil/fats including crude tall oil or tall oil fatty acids, vegetable oil/fats, animal oil/fats including fish oil/fats and algae oil/fats, or oil/fats from other microbial processes, for example genetically manipulated algae oil/fats, genetically manipulated oil/fats from other microbial processes and also genetically manipulated vegetable oil/fats, recyclable waste recyclable residue, or a combination thereof.

Components of such materials could also be used, such as for example alkyl esters (typically $C_1$-$C_5$-alkyl esters, such as methyl, ethyl, propyl, iso-propyl, butyl, sec-butyl esters).

These oils and/or fats typically comprise $C_{10}$-$C_{24}$ fatty acids and derivatives thereof, including esters of fatty acids, glycerides, i.e. glycerol esters of fatty acids.

Examples of oils include, but are not limited to rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, tallow oil, and rice bran oil, or fractions of above mentioned oils such as palm olein, palm stearin, purified tall oil, and tall oil fatty acids.

Examples of animal fats include, but are not limited to tallow, lard, yellow grease, brown grease, fish fat, poultry fat.

The fuel composition may be a middle distillate fuel composition.

By middle distillate fuel composition is meant a fuel composition where at least 90 wt % of the composition is having a boiling point from about 150° C. to 400° C. Middle distillate is a range of products that are situated between the lighter fractions and heavier products like gasoline or liquefied petroleum gas (LPG) and fuel oils. Middle distillate fuel composition includes both aviation fuel and diesel fuel. Aviation (jet) fuel may have a boiling point in the range of 150-260° C. and diesel fuel may have a boiling point in the range of 180-360° C.

Figure 4:
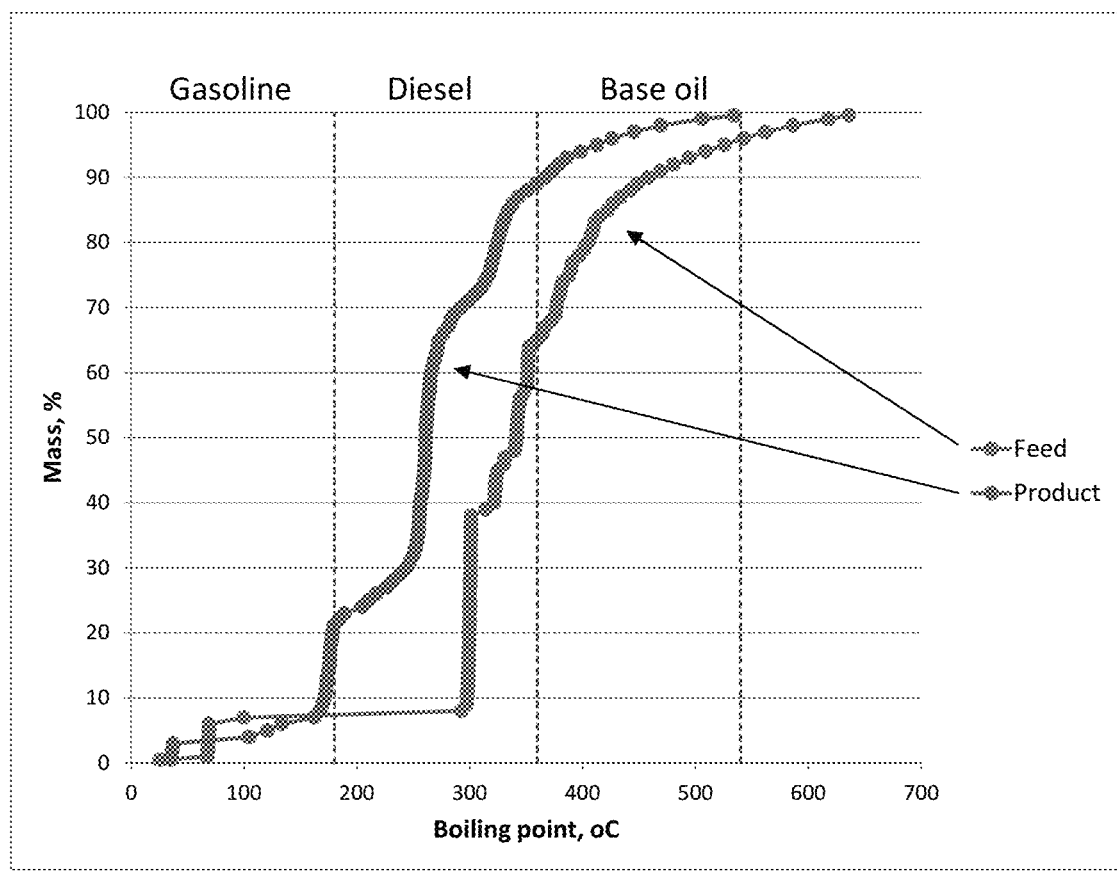
FIG. 4 shows the simulated distillation (SimDist AC620) for HDO feed (right side curve) and product (left side curve).

By the use of an acidic catalyst in the oligomerisation step followed by the use of a molybdenum and/or tungsten catalyst, optionally a promoted molybdenum and/or tungsten catalyst, optionally a sulfided molybdenum and/or tungsten catalyst, in the hydrodeoxygenation step, a fuel composition having more than 60 wt % within the boiling point range of 180-360° C. may be produced, as can be seen from FIG. 4.

More than 60 wt % of the fuel composition may have a boiling point range of 150-400° C. More than 60 wt % of the fuel composition may have a boiling point range of 180-400° C. More than 60 wt % of the fuel composition may have a boiling point range of 180-360° C.

More than 70 wt % of the fuel composition may have a boiling point range of 150-400° C. More than 70 wt % of the fuel composition may have a boiling point range of 180-400° C. More than 70 wt % of the fuel composition may have a boiling point range of 180-360° C.

More than 80 wt % of the fuel composition may have a boiling point range of 150-400° C. More than 80 wt % of the fuel composition may have a boiling point range of 180–400° C.

Almost 90 wt % of the fuel composition may have a boiling point range of 150-400° C.

Around 40 wt % of the fuel composition may have a boiling point range of 150-260° C.

The fuel composition may be a drop-in fuel composition.

By drop-in fuel composition is meant a composition that can be a fuel component as such. That is; completely interchangeable or blended with an existing fuel composition (such as a diesel hydrocarbon composition) that is; being compatible with a particular conventional fuel. In table 2 it is shown that the cloud point (measured by the ASTM D7689 method) was <−95° C., which indicates good cold flow properties of the fuel composition. Since the fuel composition has good cold flow properties it can be used directly as a drop-in fuel thereby eliminating the need for having an isomerisation step as part of the method. This is both economy saving and time saving in large fuel production plants. The fuel composition has reasonable cetane number bCN 46, and when blended with a diesel hydrocarbon composition (e.g. paraffinic renewable diesel or a gas-to-liquid (GTL) diesel) the cetane number will be above 51, which is the minimum in EN590.

It may be that no isomerisation reactions are conducted to the fuel composition. Isomerisation is normally used to achieve good cold properties, which is required especially in the Nordic countries and in Canada but the fuel composition produced by the present method may have so good cold flow properties at least in part due to the mono- and di-naphthenes and aromatics (being ring structured components) and so good density properties that isomerisation of the product may be unnecessary which means that the fuel composition can be used directly as a drop-in fuel thereby eliminating the need for having an isomerisation step as part of the method. This is both economy saving and time saving in large fuel production plants.

The fuel composition according to the present invention may be mixed/blended with a diesel hydrocarbon composition. A diesel hydrocarbon composition can be a middle distillate fuel oil boiling from about 150 to 400° C.

In some aspects no separate isomerisation reactions are required for the fuel composition admixed with a diesel hydrocarbon composition. In some aspects isomerisation reactions are done to the fuel composition admixed with a diesel hydrocarbon composition.

The diesel hydrocarbon composition that can be mixed with the produced 2MF component fuel composition may comprise at least 60 wt % hydrocarbons selected from one or both of n-paraffins or iso-paraffins boiling within the range of 180 to 360° C.

The diesel hydrocarbon composition may be paraffinic diesel. Paraffinic synthetic diesel generally has a very low content of sulfur and aromatics, and contain hydrocarbons selected from one or both of n-paraffins or iso-paraffins. Such paraffinic synthetic diesel may be obtained from biomass, and will be considered a renewable diesel.

The diesel hydrocarbon composition may be a hydrotreated vegetable oil (HVO) diesel or a gas-to-liquid (GTL) diesel.

The diesel hydrocarbon composition may be fossil diesel, which can also be called petroleum diesel or petrodiesel. It is produced from fractional distillation of crude oil to obtain a diesel fraction between 150-400° C., such as for example between 200-350° C. at atmospheric pressure.

The oligomerisation of 2-methylfuran (2-MF) in step a) may results in a furanyl containing oligomerisation composition comprising at least 80 wt. % oligomers selected from the group of trimers, tetramers and pentamers of 2-MF comprising from 2 to 4 furanyl moieties. The oligomer distribution may be trimer>>tetramer>pentamer due to the use of an acidic catalyst in the oligomerisation step and thereby controlling the degree of oligomerisation of 2-methylfuran (2-MF). Traces of oligomers higher than pentamers can also be present.

The acidic catalyst in step a) may be an acid ion exchange resin catalyst, such as a polystyrene-co-divinylbenzene sulfonic acid resin catalyst. The catalyst may be an Amberlyst 70 catalyst (from Rohm and Haas) which is an acid ion exchange resin catalyst designed for high-temperature heterogeneous catalysis. The oligomer distribution may be trimer>>tetramer>pentamer due to the use of an acidic catalyst in the oligomerisation step which control the degree of oligomerisation of 2-methylfuran (2-MF). Traces of oligomers higher than pentamers can also be present.

Hydrodeoxygenation (HDO) includes three reactions: 1) hydrogenation of oxygen bonds—removing oxygen as $H_2O$, 2) decarboxylation where oxygen is removed in the form of $CO_2$, and 3) decarbonylation where oxygen is removed in the form of CO. Many conditions for hydrodeoxygenation are known to the skilled person.

It is known to use Pt/C, Pd/C and Pt/$TiO_2$ as catalysts but is has surprisingly been shown that a more mild catalysis process is obtained when using a Mo or W based catalyst which may be promoted with one or more Group VIII non-noble metals such as Co or Ni. The catalyst may be supported on any convenient support, such as alumina, silica, zirconia, titania, amorphous carbon, molecular sieves or combinations thereof. The metal may be impregnated or deposited on the support as metal oxides and may be converted into their sulphides.

The Molybdenum and/or tungsten catalyst in step c) may be promoted with nickel or cobalt. The Molybdenum and/or tungsten catalyst in step c) may be selected from NiMo, NiW, CoMo, CoW or NiWMo catalysts. The promoted molybdenum and/or tungsten catalyst in step c) may be a sulfided NiMo-catalyst.

The hydrodeoxygenation is typically performed under a hydrogen pressure from 10-200 bar, at temperatures from 200 to 400° C., and liquid hourly space velocities of 0.2 $h^{-1}$ to 10 $h^{-1}$.

Step c) may be carried out under reaction conditions of temperature between 200-400° C., such as between 220-380° C., such as between 250-350° C., such as between 295-335° C. and at between 20 to 150 bar, such as between 60 to 120 bar, such as between 90-110 bar, such as between 95-100 bar.

The present invention also discloses a co-feed composition. Therefore, in accordance with the above description, there is also provided a composition comprising a furanyl containing oligomerisation composition comprising at least 70 wt. % oligomers selected from the group of trimers, tetramers and pentamers of 2-MF comprising from 2 to 4 furanyl moieties admixed with one or more material component comprising fatty acids or fatty acid derivatives.

The furanyl containing oligomerisation composition does not contain acids which gives the advantage that when used as a feedstock it is not a corrosive substance. Another advantage of the furanyl containing oligomerisation composition is that it is a lignocellulosic based material (originating from lignocellulosic biomass raw material) and hence a non-food material.

The inventors have found that when one or more material component comprising fatty acids or fatty acid derivatives are admixed to the furanyl containing oligomerisation composition thereby creating a co-feed composition for the following HDO treatment, the cold flow properties and the density of the fuel composition is further improved compared to when no material component comprising fatty acids or fatty acid derivatives are admixed to the furanyl containing oligomerisation composition from step a). Hydrogenated fatty acids and fatty acid derivatives are straight-chain fatty acids which have high cetane numbers so when mixing the fatty acids or fatty acid derivatives with the furanyl containing oligomerisation composition a fuel product having a relatively high cetane number can be achieved. In addition, the fuel composition arising from using the co-feed composition can have very good cold flow properties. Since the fuel composition can have excellent cold flow properties it can be used directly as a drop-in fuel thereby eliminating the need for having an isomerisation step as part of the method.

The furanyl containing oligomerisation composition differs from other feedstock material component comprising fatty acids or fatty acid derivatives selected from plant oil/fats including crude tall oil or tall oil fatty acids, vegetable oil/fats, animal oil/fats including fish oil/fats and algae oil/fats, or oil/fats from other microbial processes, for example genetically manipulated algae oil/fats, genetically manipulated oil/fats from other microbial processes and also genetically manipulated vegetable oil/fats, recyclable waste recyclable residue, or a combination thereof in at least one parameter, namely that the furanyl containing oligomerisation composition is substantially free of impurities (catalyst poisons) and hence there is no need to include any purification step such as degumming or bleaching of the furanyl containing oligomerisation composition before the hydrodeoxygenation (HDO) treatment. The material component comprising fatty acids or fatty acid derivatives may need to be purified in a purification step (e.g. by degumming or bleaching) before the hydrodeoxygenation (HDO) treatment if the material comprises too many impurities. Such impurities can e.g. be metal compounds, organic nitrogen, sulphur or phosphorous compounds. The co-feed composition preferably comprise below 10 w-ppm, preferably below 5 w-ppm and most preferably below 1 w-ppm of alkaline and alkaline earth metals and preferably comprise below 10 w-ppm, preferably below 5 w-ppm and most preferably below 1 w-ppm of other metals and preferably comprise below 30 w-ppm, preferably below 15 w-ppm and most preferably below 5 w-ppm of phosphorouos.

The majority of the trimers, tetramers and pentamers may be selected from one or more of the following components or their isomers:

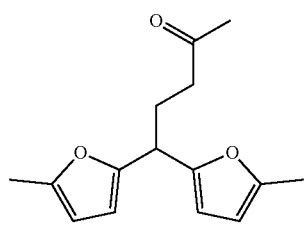

5,5-di-(5-methyl-2-furanyl)-2-pentanone
$C_{15}H_{18}O_3$ (MW 246 amu)

-continued

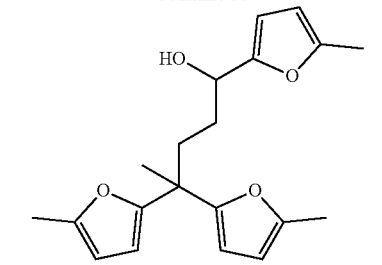

1-hydoxy-1,4,4-tri-(5-methyl-2-furanyl)-pentane,
$C_{20}H_{24}O_4$ (MW 328 amu)

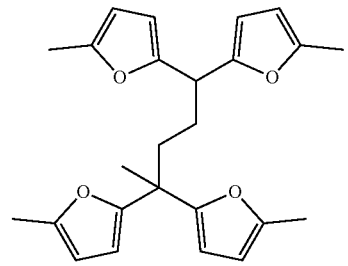

2,2,5,5-tetra-(5-methyl-2-furanyl)-pentane
$C_{25}H_{28}O_4$ (MW 329 amu)

Different isomers of these trimers, tetramers and pentamers may be possible, such as for example:

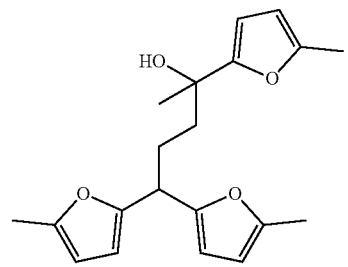

Figure 2:
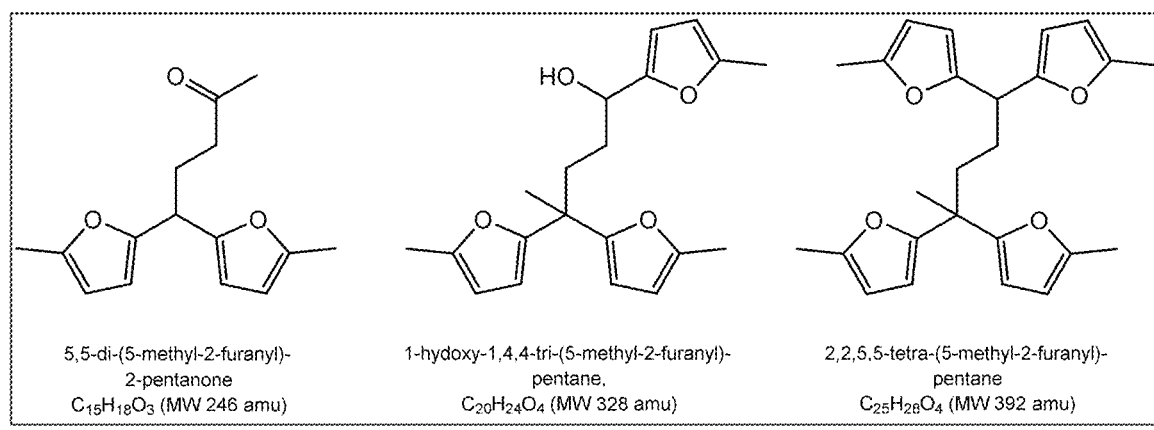
FIG. 2 shows the major trimer, tetramer and pentamer compounds identified with GC-MS from 2-methyl-furan. Different isomers of these trimers, tetramers and pentamers can also be possible and is part of the present disclosure.

By the use of an acidic catalyst in the oligomerisation step and thereby controlling the degree of oligomerisation of 2-methylfuran (2-MF)—a furanyl containing oligomerisation composition comprising at least 70 wt. % oligomers selected from the group of trimers, tetramers and pentamers of 2-MF comprising from 2 to 4 furanyl moieties was produced. FIG. 2 shows the trimers, tetramers and pentamers that represents the majority of the component being present in the composition.

The one or more material component comprising fatty acids or fatty acid derivatives may represents a majority of the composition. The composition may comprise from 50 to 90 wt. % of one or more material component comprising fatty acids or fatty acid derivatives.

The one or more material component comprising fatty acids or fatty acid derivatives may be selected from plant oil/fats including crude tall oil or tall oil fatty acids, vegetable oil/fats, animal oil/fats including fish oil/fats and algae oil/fats, or oil/fats from other microbial processes, for example genetically manipulated algae oil/fats, genetically manipulated oil/fats from other microbial processes and also genetically manipulated vegetable oil/fats, recyclable waste recyclable residue, or a combination thereof.

Components of such materials could also be used, such as for example alkyl esters (typically $C_1$-$C_5$-alkyl esters, such as methyl, ethyl, propyl, iso-propyl, butyl, sec-butyl esters).

These oils and/or fats typically comprise $C_{10}$-$C_{24}$ fatty acids and derivatives thereof, including esters of fatty acids, glycerides, i.e. glycerol esters of fatty acids.

Examples of oils include, but are not limited to rapeseed oil, canola oil, soybean oil, coconut oil, sunflower oil, palm oil, palm kernel oil, peanut oil, linseed oil, sesame oil, maize oil, poppy seed oil, cottonseed oil, soy oil, tall oil, corn oil, castor oil, jatropha oil, jojoba oil, olive oil, flaxseed oil, camelina oil, safflower oil, babassu oil, tallow oil, and rice bran oil, or fractions of above mentioned oils such as palm olein, palm stearin, purified tall oil, and tall oil fatty acids.

Examples of animal fats include, but are not limited to tallow, lard, yellow grease, brown grease, fish fat, poultry fat.

In another aspect of the present invention, there is also provided the use of a composition as presented in this application as a blending component for increasing the density of a blend composition comprising a diesel hydrocarbon composition. The diesel hydrocarbon composition can be a middle distillate fuel composition such as a paraffinic renewable diesel or a gas-to-liquid (GTL) diesel. That is, the composition as presented in this application can be used as a density improver in a middle distillate fuel composition such as a paraffinic renewable diesel or a gas-to-liquid (GTL) diesel.

By density improver is meant that by using the composition according to the present invention, the density of a middle distillate fuel composition can be improved. If the composition produced by the method according to the present invention is mixed/blended with a diesel hydrocarbon composition, the density of the final blended middle distillate fuel composition is increased compared to the density of the diesel hydrocarbon composition itself.

In table 2 it is shown that the density was 830 kg/m$^3$ (at 15° C., measured by the ENISO 12185 method), which indicates good density properties of the present fuel composition itself. When the 2MF based component of the present invention is blended/mixed with a diesel hydrocarbon composition (e.g. paraffinic renewable diesel or a gas-to-liquid (GTL) diesel) density minimum of EN590 can be reached.

In another aspect of the present invention, there is also provided the use of a composition as presented in this application as a blending component for improving the cold flow properties of a blend composition comprising a diesel hydrocarbon composition. The diesel hydrocarbon composition can be a middle distillate fuel composition such as a paraffinic renewable diesel or a gas-to-liquid (GTL) diesel. That is, the composition as presented in this application can be used as a cold flow property improver in a middle distillate fuel composition such as a paraffinic renewable diesel or a gas-to-liquid (GTL) diesel.

By cold flow property improver is meant that by using the composition according to the present invention, the cold flow property of a middle distillate fuel composition can be improved. That is, if the composition produced by the method according to the present invention is mixed/blended with a diesel hydrocarbon composition, the cold flow property of the final blended middle distillate fuel composition is improved compared to the cold flow property of the diesel hydrocarbon composition itself.

In table 2 it is shown that the cloud point (measured by the ASTM D7689 method) was <−95° C., which indicates good cold flow properties of the present fuel composition itself.

The hydrotreated oligomerized 2MF fuel composition is a good blending component that can be blended with a diesel hydrocarbon composition (e.g. paraffinic renewable diesel or a gas-to-liquid (GTL) diesel) which has excellent cold flow properties and cetane number. When blending the fuel composition manufactured according to the present method with a diesel hydrocarbon composition (e.g. paraffinic renewable diesel or a gas-to-liquid (GTL) diesel), the two components complement each other giving the blend composition increased density compared to the diesel hydrocarbon composition itself. In addition, the blend composition will also have improved cold flow properties and a good cetane number.

In another aspect of the present invention, there is also provided the use of a furanyl containing oligomerisation composition comprising at least 70 wt. % oligomers selected from the group of trimers, tetramers and pentamers of 2-MF comprising from 2 to 4 furanyl moieties as a co-feed in an existing refinery hydro-treating unit.

By co-feed is meant that the furanyl containing oligomerisation composition comprising at least 70 wt. % oligomers selected from the group of trimers, tetramers and pentamers of 2-MF comprising from 2 to 4 furanyl moieties can be co-processed together with one or more material component comprising fatty acids or fatty acid derivatives in an existing refinery hydrotreating unit.

The inventors have found that when one or more material component comprising fatty acids or fatty acid derivatives are admixed to the furanyl containing oligomerisation composition thereby creating a co-feed composition for the following HDO treatment, the cold flow properties and the density of the fuel composition may be further improved compared to when no material component comprising fatty acids or fatty acid derivatives are admixed to the furanyl containing oligomerisation. When mixing the fatty acids or fatty acid derivatives with the furanyl containing oligomerisation composition a fuel product having a relatively high cetane number can be achieved. In addition, the fuel composition arising from using the co-feed composition can have very good cold flow properties. Since the fuel composition can have excellent cold flow properties it can be used directly as a drop-in fuel. Additionally there might be no need for isomerisation.

The furanyl containing oligomerisation composition differs from other feedstock material component comprising fatty acids or fatty acid derivatives selected from plant oil/fats including crude tall oil or tall oil fatty acids, vegetable oil/fats, animal oil/fats including fish oil/fats and algae oil/fats, or oil/fats from other microbial processes, for example genetically manipulated algae oil/fats, genetically manipulated oil/fats from other microbial processes and also genetically manipulated vegetable oil/fats, recyclable waste recyclable residue, or a combination thereof in at least one parameter, namely that the furanyl containing oligomerisation composition is substantially free of impurities (catalyst poisons) and hence there is no need to include any purification step such as degumming or bleaching of the furanyl containing oligomerisation composition before the hydrodeoxygenation (HDO) treatment. The material component comprising fatty acids or fatty acid derivatives may need to be purified in a purification step (e.g. by degumming or bleaching) before the hydrodeoxygenation (HDO) treatment if the material comprises too many impurities. Such impurities can e.g. be metal compounds, organic nitrogen, sulphur or phosphorous compounds. The co-feed composition preferably comprise below 10 w-ppm, preferably below 5 w-ppm and most preferably below 1 w-ppm of alkaline and alkaline earth metals and preferably comprise below 10 w-ppm, preferably below 5 w-ppm and most preferably below 1 w-ppm of other metals and preferably comprise below 30 w-ppm, preferably below 15 w-ppm and most preferably below 5 w-ppm of phosphorouos.

The use of the furanyl containing oligomerisation composition comprising at least 70 wt. % oligomers selected from the group of trimers, tetramers and pentamers of 2-MF comprising from 2 to 4 furanyl moieties as feedstock is broadening the narrow hydrocarbon distribution originating from the hydrocarbon distribution of the one or more material component comprising fatty acids or fatty acid derivatives in the existing refinery hydrotreating unit.

In accordance with the above description, there is also provided a fuel composition obtainable by the method according to the present invention.

In accordance with the above description, there is also provided a blend composition, the blend composition comprises a fuel composition obtainable by the method according to the present invention and a diesel hydrocarbon composition.

The hydrotreated oligomerized 2MF fuel composition produced by the method according to this invention is a good blending component that can be blended with a diesel hydrocarbon composition (e.g. paraffinic renewable diesel or a gas-to-liquid (GTL) diesel) which has excellent cold flow properties and cetane number. When blending the fuel composition manufactured according to the present method with a diesel hydrocarbon composition (e.g. paraffinic renewable diesel or a gas-to-liquid (GTL) diesel), the two components complement each other giving the blend composition increased density compared to the diesel hydrocarbon composition itself. In addition, the blend composition will also have improved cold flow properties and a good cetane number.

The diesel hydrocarbon composition can be a middle distillate fuel oil boiling from about 150 to 400° C. The diesel hydrocarbon composition that can be mixed with the produced 2MF component fuel composition may comprise at least 60 wt % hydrocarbons selected from one or both of n-paraffins or iso-paraffins boiling within the range of 180 to 360° C.

The diesel hydrocarbon composition may be paraffinic diesel. Paraffinic synthetic diesel generally has a very low content of sulfur and aromatics, and contain hydrocarbons selected from one or both of n-paraffins or iso-paraffins. Such paraffinic synthetic diesel may be obtained from biomass, and will be considered a renewable diesel.

The diesel hydrocarbon composition may be a hydrotreated vegetable oil (HVO) diesel or a gas-to-liquid (GTL) diesel.

The diesel hydrocarbon composition may be fossil diesel, which can also be called petroleum diesel or petrodiesel. It is produced from fractional distillation of crude oil to obtain a diesel fraction between 150-400° C., such as for example between 200-350° C. at atmospheric pressure.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

Example 1 (Oligomerisation of 2-methylfuran (2-MF))

The reactant used in this example was commercial 2-methylfuran (Sigma-Aldrich, ≥98%) with density 927 kg/m³ and boiling point 63-66° C.

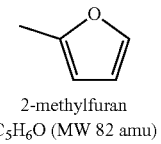

2-methylfuran
$C_5H_6O$ (MW 82 amu)

Oligomerisation of 2-methylfuran (2-MF) was carried out in batch reactor at 70° C. The acid ion exchange catalyst used, Amberlyst 70, was wetted with a small amount of water before adding 2-MF into the reactor. The batch experiment was repeated three times in order to produce the feed needed for the subsequent oxygen removal step. The reaction conditions used is shown in Table 1.

TABLE 1

Reaction conditions for the oligomerisation of 2-MF in batch reactor.

| Entry | T, ° C. | p, bar | Time, h | 2-MF, g | $H_2O$, g | Catalyst, g |
|---|---|---|---|---|---|---|
| 1 | 71 | 1-2 | 125 | 343.9 | 5.0 | 12.0 |
| 2 | 73 | 1-2 | 122 | 347.5 | 5.0 | 12.0 |
| 3 | 72 | 1-2 | 96 | 316.3 | 5.0 | 12.0 |

The final product distribution was determined by GPC. Compounds formed were identified by GC-MS.

Oligomer Formation

Primary and secondary oligomerisation products from 2-methylfuran (82 amu (atomic mass unit)) with following molecular weights (amu) was identified by GC-MS (FIG. 1):
trimers: 244, 246, 262, 264, 266, 286
tetramers: 310, 316, 328, 346, 354
pentamers: 392, 410

The main trimer compound produced was the primary oligomerisation product with molecular weight 246 (3×82) amu. For tetramers and pentamers two major compounds were identified: the primary oligomerisation product (328=4×82 amu and 410=5×82 amu). Proposed structures for major trimer, tetramer and pentamer compounds are shown in FIG. 2—other isomers may also exist.

Figure 3:
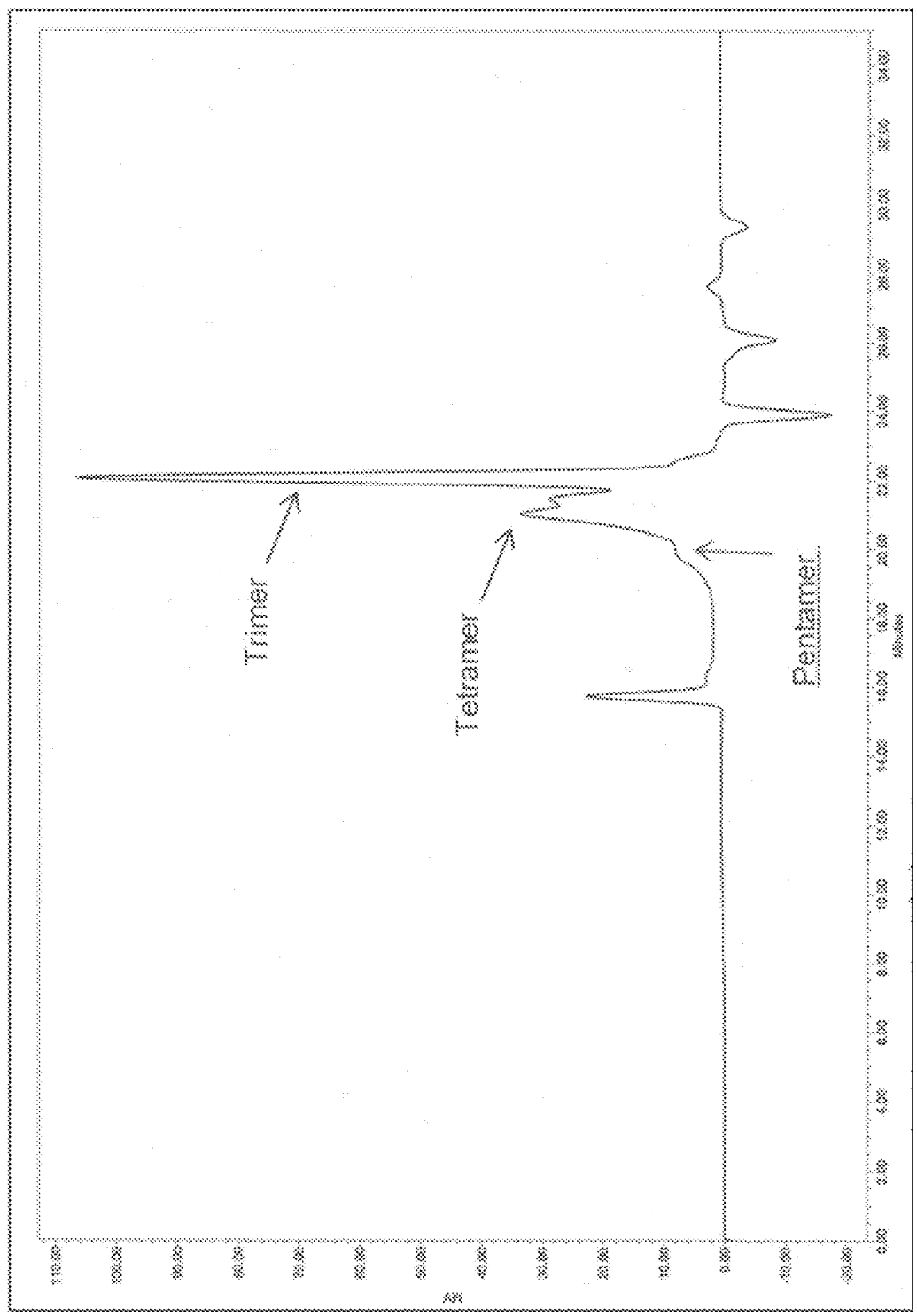
FIG. 3 shows the GPC of oligomer mixtures produced from 2-MF (combined product sample from the three batch experiments) where it can be seen that the oligomer distribution is trimer (the highest top around 22 minutes)>>tetramer (the second highest top around 21 minutes)>pentamer (the "shoulder" around 20).

According to GPC (FIG. 3) the oligomer distribution is trimer>>tetramer>pentamer. Traces of oligomers higher than pentamers were also observed.

Example 2 (Hydrodeoxygenation of the Oligomer Product from Example 1)

Hydrodeoxygenation of the oligomer product formed (without removing unreacted 2-MF) was carried out in continuous laboratory scale tubular reactor with a sulfided NiMo-catalyst. The density of the oligomerisation feed, i.e. the combined oligomerisation product from the three batch runs, was 1102 kg/m³. The distillation curve of the feed was analysed by SimDist AC620, the product distribution by GPC and the product composition by GC-MS and IR.

A NiMo-catalyst (24.2 g) was diluted with SiC in the ratio 1:1 (30 ml/30 ml). The reaction temperature formed a gradient over the catalyst bed starting with a lower temperature at the inlet. The maximum temperature was 335° C. and the average temperature over the whole catalyst bed 295° C. The oligomer product was fed into the reactor at WHSV 0.66 $h^{-1}$ (16.1 g/h) and the hydrogen flow rate was 23.8 l/h. The reaction pressure in the reactor was in average 97 bar.

Hydrodeoxygenation of Oligomer Product

According to FTIR the HDO product consisted mainly of paraffinic hydrocarbons and some aromatic components—no oxygen containing components were observed in the spectra. The only oxygenated compounds identified by GC-MS were C4-, C9- and C14-phenols, but in very small amounts. The reduction of the density from 1102 kg/m³ in the feed to 820-830 kg/m³ in the product further support the success of the oxygen removal. Simulated distillation curves for the HDO feed and product is compared in FIG. 4 showing the shift to lower boiling products due to oxygen removal.

From the simulated distillation (FIG. 4) it is seen that about 20 wt-% of the HDO product is in the gasoline range, 70 wt-% in the middle distillate range and 10 wt-% in the base oil range.

Figure 5:
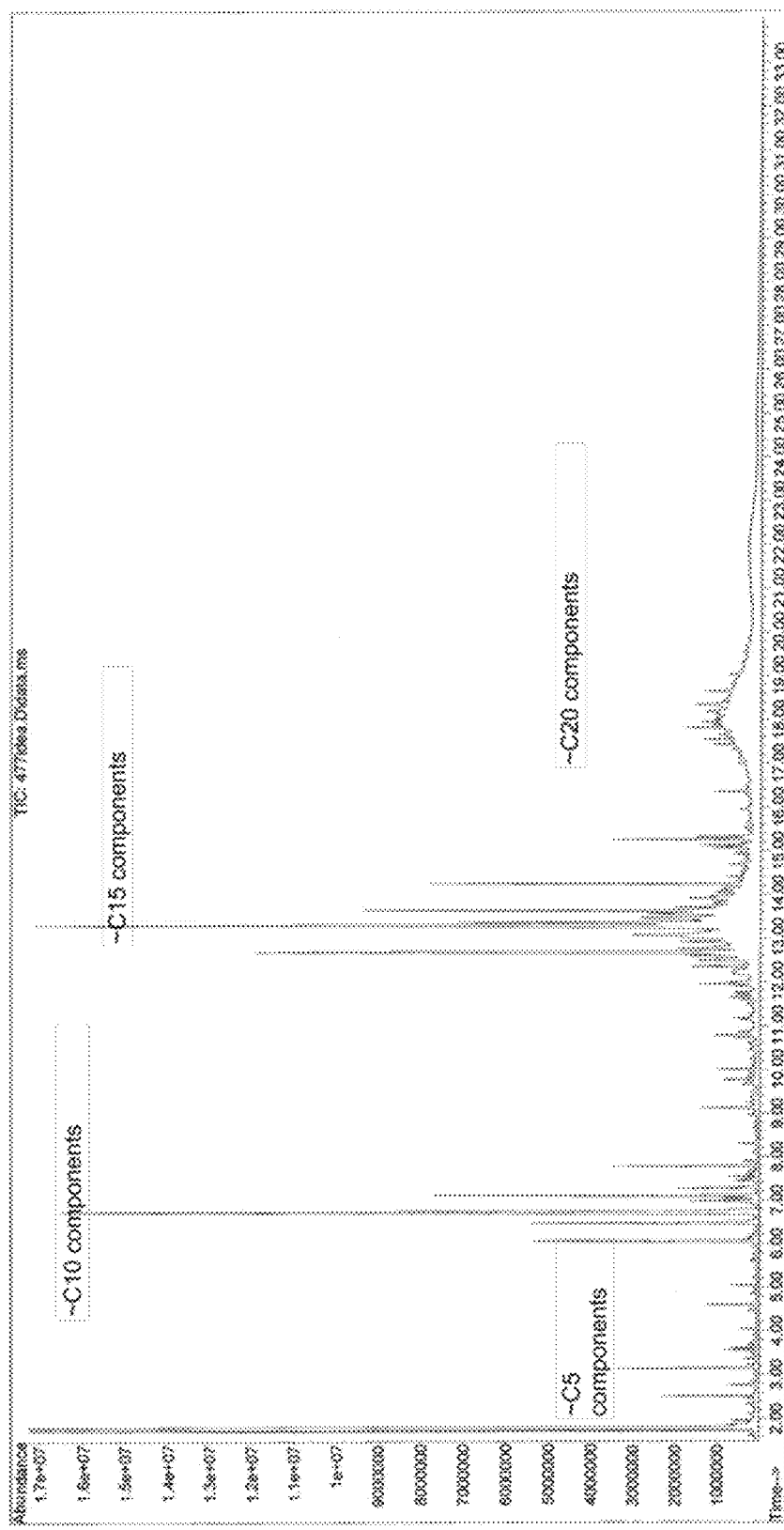
FIG. 5 shows the GC-MS identification of HDO products obtained with sulfided NiMo-catalyst.
Figure 6:
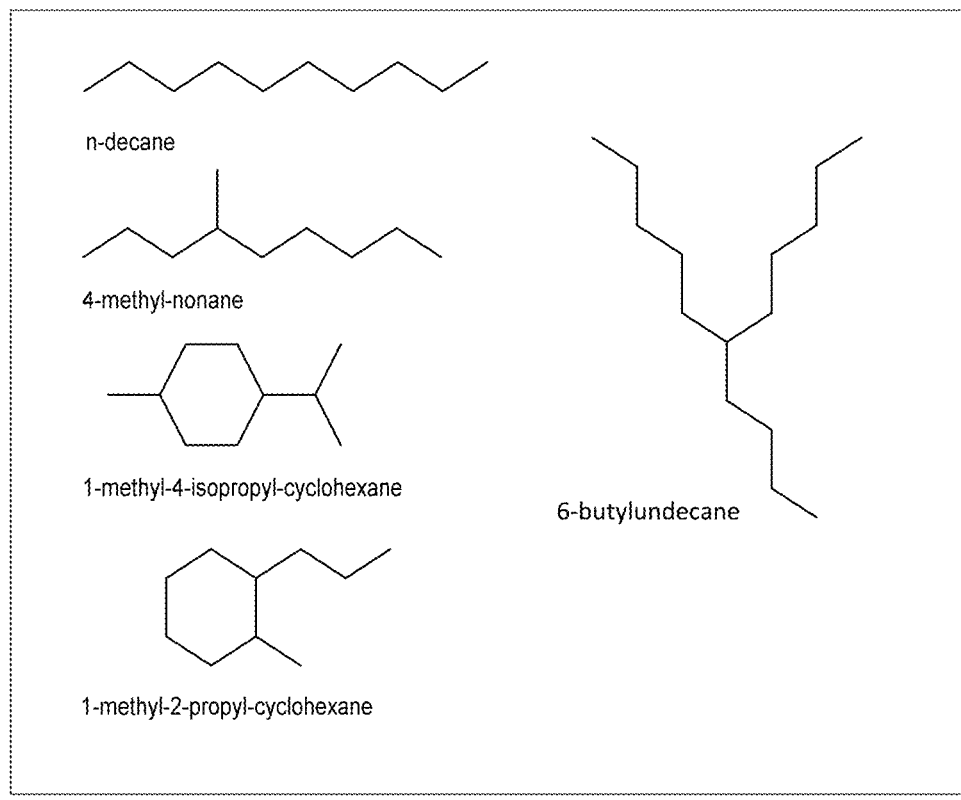
FIG. 6 shows examples of major C10 and C15 paraffinic hydrocarbon components in the HDO product.

According to GC-MS analysis (FIG. 5) the HDO product consisted of a complex mixture of mainly naphthenes (mono- and dinaphthenes) and aromatics (alkylbenzenes, indanes, naphthalenes) within a wide boiling range (MW 58 to about 400 amu). Three maximum in the distribution of hydrocarbon components was observed at carbon numbers ~C10, ~C15 and ~C20. This grouping of the components into three boiling point ranges is also seen the simulated distillation curve. Examples of major C10 and C15 paraffinic hydrocarbon components are shown in FIG. 6.

Example 3 (Product Properties)

Selected diesel fuel properties were analysed from the HDO product sample described above. Cloud point was excellent offering extra value in blending. As a result of cyclic molecular structures and some gasoline range hydrocarbons the cetane number was reasonable i.e. some 46.

TABLE 2

Selected diesel analysis from HDO product sample.

| Property | Method | Result |
|---|---|---|
| Density at 15° C., kg/m³ | ENISO 12185 | 829.6 |
| Cloud point, ° C. | ASTM D7689 | <-95 |
| Sulphur, mg/kg | ASTM D7039 | 3.4 |
| HFRR, µm | ENISO 12156-1 | 523 |
| bCN* | ASTM D6890 | 46 |

*Blending cetane number is calculated from the cetane number of the blend containing 30% product sample and 70% fossil winter grade diesel.

The invention claimed is:

1. A method for production of a fuel composition, the method comprising:
    a) oligomerisation of 2-methylfuran (2-MF) using an acidic catalyst resulting in a furanyl containing oligomerisation composition having at least 70 wt. % oligomers selected from the group consisting of trimers, tetramers and pentamers of 2-MF having from 2 to 4 furanyl moieties;
    b) optionally admixing one or more material components containing fatty acids or fatty acid derivatives to the furanyl containing oligomerisation composition from step a) creating a co-feed composition;
    c) subjecting the furanyl containing oligomerisation composition from step a) or the co-feed composition from step b) to a hydrodeoxygenation treatment in a hydrodeoxygenation unit containing a molybdenum and/or tungsten catalyst, optionally a promoted molybdenum and/or tungsten catalyst, optionally a sulfided molybdenum and/or tungsten catalyst, resulting in a fuel composition;
    where said fuel composition contains at least 55 wt. % of both mono- and di-naphthenes and aromatics in a part of the fuel composition resulting from the hydrodeoxygenation treatment of the furanyl containing oligomerisation composition.

2. The method according to claim 1, where step b is mandatory.

3. The method according to claim 1, where the fuel composition is a middle distillate fuel composition.

4. The method according to claim 1, where the fuel composition is a drop-in fuel composition.

5. The method according to claim 1, where the one or more material components containing fatty acids or fatty acid derivatives are selected from the group consisting of plant oil/fats, crude tall oil, tall oil fatty acids, vegetable oil/fats, animal oil/fats, fish oil/fats, algae oil/fats, oil/fats from microbial processes, genetically manipulated algae oil/fats, genetically manipulated oil/fats from microbial processes, genetically manipulated vegetable oil/fats, recyclable waste, recyclable residue, and a combination thereof.

6. The method according to claim 1, where the oligomerisation of 2-methylfuran (2-MF) in step a) results in a furanyl containing oligomerisation composition comprising:
    at least 80 wt. % oligomers selected from the group consisting of trimers, tetramers and pentamers of 2-MF comprising from 2 to 4 furanyl moieties.

7. The method according to claim 1, where more than 60 wt % of the fuel composition has a boiling point range of 150-400° C.

8. The method according to claim 1, where no isomerisation reactions are conducted to the fuel composition.

9. The method according to claim 1, where the acidic catalyst in step a) is a polystyrene-co-divinylbenzene sulfonic acid resin catalyst, or any acid ion exchange resin catalyst.

10. The method according to claim 1, comprising:
    promoting the molybdenum and/or tungsten catalyst in step c) with nickel or cobalt.

11. The method according to claim 10, where the promoted molybdenum and/or tungsten catalyst in step c) is a sulfided NiMo-catalyst.

12. The method according to claim 1, comprising:
    performing step c) under reaction conditions with a temperature between 200-400° C. and between 20 to 150 bar.

* * * * *